(12) United States Patent
Kämpf et al.

(10) Patent No.: US 7,482,584 B2
(45) Date of Patent: Jan. 27, 2009

(54) METHOD FOR THE AUTOMATIC ANALYSIS OF REFUSE CONTAINING POLYMERS AND AN AUTOMATIC ANALYTICAL DEVICE FOR THIS PURPOSE

(75) Inventors: Rudolf Kämpf, Haingründau (DE); Reinhard Wolf, Rodenbach (DE)

(73) Assignee: Lurgi Zimmer GmbH, Frankfurt (DE)

( * ) Notice: Subject to any disclaimer, the term of this patent is extended or adjusted under 35 U.S.C. 154(b) by 0 days.

(21) Appl. No.: 10/959,732

(22) Filed: Oct. 6, 2004

(65) Prior Publication Data
US 2005/0127285 A1     Jun. 16, 2005

(30) Foreign Application Priority Data
Oct. 6, 2003     (DE) ................. 103 46 768

(51) Int. Cl.
*H01J 49/04* (2006.01)
*G01N 1/24* (2006.01)
*B29B 17/00* (2006.01)

(52) U.S. Cl. .................. 250/288; 250/282; 250/281

(58) Field of Classification Search ................. None
See application file for complete search history.

(56) References Cited

U.S. PATENT DOCUMENTS

| | | | |
|---|---|---|---|
| 3,959,341 A | 5/1976 | Dunn | |
| 4,448,943 A | 5/1984 | Golba, Jr. et al. | |
| 4,680,376 A | 7/1987 | Heinze et al. | |
| 5,045,694 A | 9/1991 | Beavis et al. | |
| 5,134,291 A | 7/1992 | Ruhl, Jr. et al. | |
| 5,155,184 A | 10/1992 | Laurent et al. | |
| 5,208,544 A | 5/1993 | McBrearty et al. | |
| 5,216,149 A * | 6/1993 | Evans et al. | 540/538 |
| 5,256,880 A | 10/1993 | Loree et al. | |
| 5,359,061 A | 10/1994 | Evans et al. | |
| 5,510,619 A | 4/1996 | Zachmann et al. | |
| 5,512,752 A | 4/1996 | Aikawa et al. | |
| 5,872,205 A | 2/1999 | Balke et al. | |
| 6,188,064 B1 | 2/2001 | Koster | |
| 6,465,776 B1 | 10/2002 | Moini et al. | |
| 2002/0128335 A1 | 9/2002 | Kumai et al. | |

FOREIGN PATENT DOCUMENTS

DE     3544551     6/1987

(Continued)

OTHER PUBLICATIONS

Search Report for German Application No. 103 46 768.8 dated Oct. 6, 2003.

*Primary Examiner*—Jack I Berman
(74) *Attorney, Agent, or Firm*—Michael Best & Friedrich LLP

(57) ABSTRACT

The invention relates to a method for the analysis of refuse objects (2) containing polymers, in particular of carpets, in a recycling plant (1) and an automatic analytical device (7). In order to determine the polymer constituents of the refuse object (2), according to the invention, part of the refuse object (2) is vaporised and examined by a mass spectrometer (18). Using the method according to the invention and the automatic analytical device according to the invention, the refuse objects (2) can be classified for further processing (9, 10, 11) more accurately and more reliably during transport on a conveyor device (6).

30 Claims, 5 Drawing Sheets

FOREIGN PATENT DOCUMENTS

| | | |
|---|---|---|
| DE | 3926641 | 2/1991 |
| DE | 4200497 | 7/1993 |
| DE | 4200497 A1 * | 7/1993 |
| DE | 19934349 | 1/2001 |
| EP | 0306307 | 3/1989 |
| EP | 0376119 | 7/1990 |
| EP | 0572848 | 12/1993 |
| EP | 0579055 | 1/1994 |
| EP | 0594887 | 5/1994 |
| EP | 0700458 | 3/1996 |
| EP | 1122293 | 8/2001 |
| EP | 1280185 | 1/2003 |
| WO | WO 98/019800 | 5/1998 |
| WO | WO 98/53909 | 12/1998 |
| WO | WO 01/21560 | 3/2001 |
| WO | WO 01/36087 | 5/2001 |
| WO | WO 2005/036166 | 4/2005 |

* cited by examiner

METHOD FOR THE AUTOMATIC ANALYSIS OF REFUSE CONTAINING POLYMERS AND AN AUTOMATIC ANALYTICAL DEVICE FOR THIS PURPOSE

RELATED APPLICATIONS

This application claims the foreign priority of German Patent Application No. 103 46 768.8 filed on Oct. 6, 2003, the entire contents of which are hereby incorporated by reference.

The invention relates to a method by which refuse objects containing polymers, such as for example carpets, are analysed during transport with regard to the polymers they contain before recycling. The invention also relates to an automatic analytical device with a probe by which the refuse objects containing polymers are analysed.

The recycling of synthetics or plastics, in particular of polymers, from industrial and household refuse is becoming increasingly important due to legal regulations. One such legal regulation, for example, forms the basis of the returnable bottle system in the beverage industry in which bottles of polyethylene terephthalate (PET) are recycled. Using a controlled collection system, the same type of bottle-refuse with documented origin is collected and reutilised. The returnable bottle system presents no problem with respect to the technical requirements of reutilisation, because only a single type of plastic, i.e. polyethylene terephthalate, comes up and has to be recycled. This facilitates the specific use of methods adapted to the properties of polyethylene terephthalate, for example, to clear the PET bottles of contamination. According to EP-A-0 376 119 a supercritical carbon dioxide can, for example, be used for cleaning bottles of polyethylene terephthalate.

The same applies to other fields in which refuse objects are recycled from two single types of plastic. As an example here, the method of US-A-2002 0128335 is mentioned which can be used exclusively for the recovery of fluorine polymers.

However, in contrast to the single types of plastic, the plastic refuse normally arising in households and in industry is a mixture of different plastics and polymers or is contaminated, so that the recyclates obtained from these mixtures no longer exhibit the properties of the initial raw products. The equipment and methods to be employed with these types of refuse objects for reutilisation are substantially more complex than the equipment and methods for the reutilisaton of plastics of a single type.

In terms of quantity, a relatively large refuse group of a mixture of different polymers is represented by, for example, fitted carpets, the reprocessing of which is to date not subject to any legal regulation. During the renovation of public and private rooms after a period of use of about five to nine years large quantities of used carpets arise on an almost rotational basis as well as cuttings waste with newly laid carpets which should be passed on for recyclable material recovery. An efficient practicable recovery assumes however separation of the carpet materials into the individual components. For example, the largest part of fitted tufted carpets consists of polymer fibres of polyamide 6, polyamide 6,6, polyethylene terephthalate, polybutylene terephthalate or of polypropylene for the more inexpensive types. The pile produced from these fibres is applied to a carrier material or tufted substrate of polypropylene and/or natural fibre fabric. The carpet backing, which comes into contact with the floor, consists of a styrol-butadiene latex foam filled with chalk or inorganic additive materials and provides impact sound insulation. Dual backings have recently started to be produced from polypropylene or natural fibre fabric only without foam backings. The carpet residues for disposal may also contain substantial amounts of various contaminants, such as soil, street dust, carpet adhesive, cleaning agents, food residues, etc. Occasionally during sorting and visual assessment, carpet remnants arise which, due to heavy contamination, are found to be unsuitable for reprocessing and are incinerated.

From an economical viewpoint, the recovery of polymers from the materials in refuse objects, which are passed to the recycling circuit, by cracking into the raw materials, their purification and ensuing polymerisation into new polymers is of primary interest. This type of recovery method should be capable of recovering the monomers in such a pure state that they can be used for the synthesis of polymers in the same way as a fresh raw material. An overview of the thermal decomposition methods and pyrolysis methods with which such recycling can be carried out may be found, for example, in EP-A-1 122 293 and in U.S. Pat. No. 5,359,061.

A further method of recovering polymers is described in U.S. Pat. No. 5,872,205 in which refuse materials of a polymer mixture are separated based on the different viscosity of the individual polymers in a polymer melt. However, as stated also in this publication, a complete separation of the polymers solely based on their different melt viscosities is not possible and some contamination of the separated polymers always remains.

A range of analytical methods is based on the examination of the reflection or absorption properties of the refuse objects in the infrared range in order to separate the refuse appropriately to the contained polymers.

Consequently, U.S. Pat. No. 5,134,291 describes the use of scattered light in the near infrared range to classify the refuse objects into groups of similar polymers. An exact classification of the polymers for achieving qualitatively high-grade recyclates is however not possible with this method.

According to U.S. Pat. No. 5,512,752, the absorption spectrum is measured in the near infrared range of an unknown plastic. To determine the plastic the absorption spectrum and the first and second derivatives of the absorption spectrum are compared with stored values.

A similar procedure is used with the method according to U.S. Pat. No. 5,510,619, where the reflection spectrum is acquired in the medium infrared range to identify plastics. Here, the first derivative with respect to the wave number is formed from the acquired infrared spectrum and compared with the first derivative of a reference infrared spectrum.

Apart from infrared spectra, fluorescence spectra and UV induced emission spectra are used for the identification of plastics, as described in U.S. Pat. No. 5,256,880.

In WO-A-98 019800, which in view of the applicant represents the most clearly related prior art, a sorting method for plastic refuse is described which is based on an evaluation of the spectrum of Raman scattering. However, with this method, as is the case with the infrared-based methods, a disadvantage is that, for example, polyamide 6 and polyamide 6,6 cannot be differentiated due to their very similar spectra or can only be differentiated with enormous effort and a high error quota. Despite complex and costly analysis methods, this causes operational malfunction and losses of quality in the recyclates in the following processing stages, such as for example cracking or compounding.

The object of the invention is therefore to provide a method with which the synthetics or plastics contained in refuse, in particular in rugs and carpets, can be reliably and accurately identified in a recycling plant in order to be able to sort them and to obtain recyclates of high quality.

This object is solved according to the invention for the method mentioned at the beginning in that a part of the refuse object is converted into the gaseous state and the gas thus obtained is examined mass spectroscopically by a mass spectrometer.

This solution is simple and avoids the problems associated with the optical analysis of reflection and absorption spectra or of fluorescence and Raman spectra, because the polymer constituents of the refuse object can be analysed at a low expense and high reliability and in real time through the mass spectroscopic examination. The refuse objects can then be sorted in dependence of the analysis.

The functioning principle of mass spectroscopy is for example described in: D. A. Skoog and J. J. Leary, "Instrumentelle Analytik" (Instrumental Analysis), Springer-Verlag, Berlin, Heidelberg, New York, 1996. This reference is herewith expressly incorporated into the disclosure.

The use of mass spectroscopy within the scope of the solution according to the invention differs significantly from the usual field of use for mass spectroscopy, such as for example is known from EP-A-1 122 993 and U.S. Pat. No. 5,359,061. There, mass spectroscopic examination is only used to check randomly the result of the pyrolysis. In contrast to this use mass spectroscopy is employed according to the invention for the continuous monitoring and classification of refuse passed to a recycling plant before it is recycled so that a reliable and accurate sorting of the waste according to the polymers contained therein can take place.

The above mentioned object is solved also by an automatic analytical device or analysis automat which is designed for installation in a plant for the recycling of refuse objects, containing polymers, such as carpets, so that existing plants can be retrofitted. The automatic analytical device comprises a probe with a vaporisation device and a gas line, whereby part of the refuse object to be recycled can be vaporised to a gas by the vaporisation module and whereby the gas line is adapted for connection to a mass spectrometer and the gas can be passed through the gas line to the mass spectrometer for the acquisition of a mass spectrum. The automatic analytical device according to the invention also comprises an evaluation unit which can be connected to the mass spectrometer for data transfer and by which a signal can be output representing the composition of the polymer in dependence of the acquired mass spectrum.

The advantage of mass spectroscopy in the analysis of the refuse objects is in particular that the mass spectrum of a plastic mixture measured by the mass spectrometer is only an addition of the individual mass spectra of the constituents of these plastics. Consequently, the compositions of the refuse objects that are transported through the recycling plant and analysed by the mass spectrometer can be determined with little computational effort by simply solving linear equation systems. The evaluation method can therefore be carried out quickly enough so that the constituents can be determined during the transport of the refuse objects through the plant and they can be passed to processing stages corresponding to their constituents. In this way the method according to the invention and the automatic analytical device according to the invention are capable of a running analysis of the refuse objects transported through the recycling plant in a continuous mode during the transport of the refuse objects.

The mass spectrometer can in particular be calibrated to certain types of refuse objects, such as for example carpets, in that mass spectra of the individual constituents or fragments of refuse objects are saved or stored as calibration spectra in the evaluation unit. In dependence of the comparison of the measured spectrum with the saved calibration spectra, the composition of the refuse object can then be analysed.

In the following, various advantageous improvements of the method according to the invention and of the automatic analytical device according to the invention are described. The various embodiments can be used independently of one another in any combination.

For example, the speed of the evaluation process can be increased in that only the maxima or peaks of the measured mass spectra are compared with the maxima or peaks of the calibration spectra. Through this measure the comparison is reduced to a few data points, so that only little computing effort needs to be provided for the identification of the polymers contained in a refuse object.

Since the composition of the plastics arising in a recycling plant can exhibit a wide bandwidth, it is an advantage according to one embodiment if in the course of the mass spectroscopic examination, mass spectra are acquired over a range of 1 amu (atomic mass unit) up to 5,000 amu, preferably 1 amu to 2,000 amu or 1 amu to 1,000 amu.

A further range of advantageous embodiments involves the gas line with which the vaporised gas of the refuse object to be analysed is passed to the mass spectrometer. For example, it can be an advantage if the gas line is heated.

In particular the temperature of the gas line can be at least 10° C. above the melting point of the polymer or of the component with the highest melting temperature, so that no solids can be deposited in the gas line. The risk of deposits can, according to an advantageous further development, also be reduced in that the temperature of the gas line is at least 70° C. above the melting point of the polymer or of the component with the highest melting point.

If the formation of condensate in the gas line to the mass spectrometer is to be avoided, then the temperature of the line can be above the condensation temperature of the gas passed to the mass spectrometer. This temperature can, for example, be at least 250° C.

According to a further embodiment, a dilution gas flow of nitrogen or helium can be added to the gas in the gas line to the mass spectrometer to reduce the concentration of the gas.

In order not to influence subsequent measurements, according to a further range of advantageous embodiments, a flushing device can be provided by which the gas line is cleaned after extracting a sample. In this way it can be ensured that the measurements are not influenced by deposits or contaminations from previous sample extractions.

This sort of cleaning can, for example, occur by heating the line such that residues on the line and in the interior of the line are incinerated and the following measurement can no longer be influenced. Alternatively or additionally to cleaning using heating, a flushing gas can also be passed through the line, preferably an inert gas such as helium or nitrogen. The flushing gas can also have a high temperature by which the residues in the line are incinerated. In particular, the temperature of the flushing gas can be set as above in the case of the temperature of the gas line, i.e. for example also above the condensation limit of the gas.

In order to carry out the method without any interruption, despite the cleaning of the line, during the transport of the refuse objects past the probe or the automatic analytical device, according to another advantageous embodiment at least two probes are provided which alternately extract a gas sample from the refuse objects transported past the automatic analytical device. In particular with this embodiment, one probe can be automatically cleaned while the other probe carries out the measurement.

A calibration of the automatic analytical device can preferably occur in that the mass spectra of all known polymers of the refuse objects occurring, especially in carpets, and of the decomposition products occurring during the vaporisation are measured many times with various heating rates on the vaporisation device and are saved or stored as calibration spectra in the automatic analytical device. If the mass spectrum of a refuse object is measured during the operation of the recycling plant, it is then compared with the saved calibration spectra and the calibration spectrum then selected whose deviation is lowest from the measured mass spectrum. The deviation can, for example, be computed in the form of the sum of the square error over the mass spectrum.

Since the selected calibration spectrum is representative for a certain polymer composition, the composition of the refuse object can be determined such that the refuse object is sorted depending on the result of the mass spectroscopic examination. In an alternative or additional method the calibration spectra are determined in the form of fragmentation spectra, whereby a single fragmentation spectrum corresponds to constituents of a certain polymer. With this method calibration or fragmentation spectra are sought which add up to the measured mass spectrum. The fragmentation spectra of the individual polymers are appropriately weighted in the mass spectrum according to the proportion of the polymer in the refuse object. In contrast to the previous method, with this method the composition of the refuse object is analysed. The refuse object can then be classified in dependence of the analysis.

In the following the invention is exemplarily explained in more detail based on different embodiments with reference to the drawings. Hereby, the same reference symbols are used in the various embodiments for features of the same design or of the same function.

As became clear from the previous description of the advantages associated with the individual features, the features of the various embodiments can be combined as desired and individual features of the embodiments can also be completely omitted.

Figure 1:
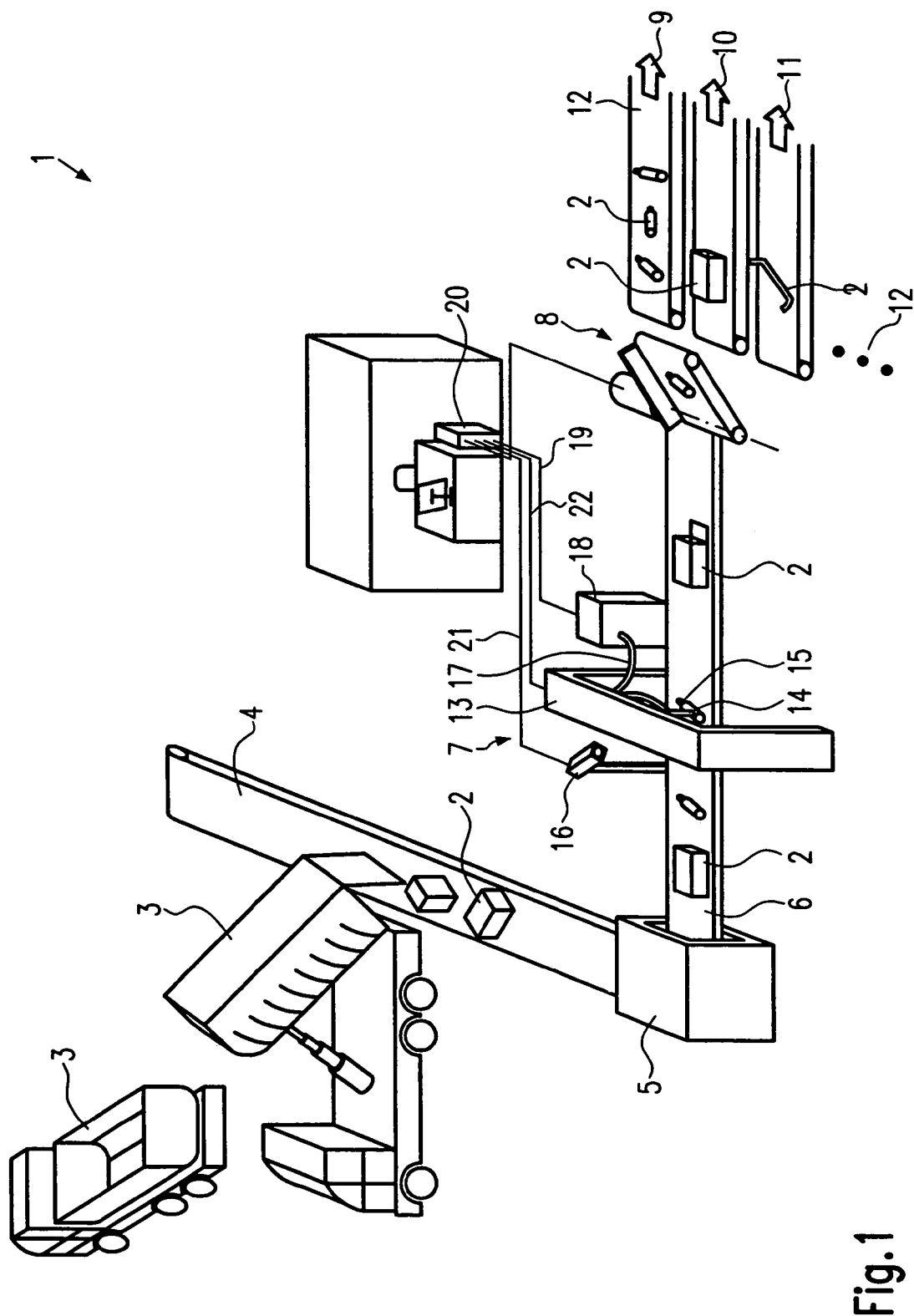
FIG. 1 shows a first embodiment of a refuse recycling plant with an automatic analytical device according to the invention in a schematic illustration.

FIG. 1 shows schematically a section of a plant 1 for the recycling of plastic refuse 2 containing polymers, which, for example is brought pre-sorted, i.e. free of refuse containing non-plastics, by truck 3 from a collection point. The plastic refuse 2 is conveyed by a conveyor belt from the truck 3 to a device 5 through which the refuse objects 2 are collected and aligned on a further conveyor belt 6. The conveyor belt 6 is equipped with an automatic analytical device 7 according to the invention which determines the composition of the refuse objects 2 and which operates a sorting device 8, for example in the form of switching points, in dependence of their composition. The refuse objects 2 are passed by the sorting device 8 in dependence of their composition and the polymers they contain to various recovery and processing methods, as indicated by the arrows 9, 10, 11.

For example, bottles of polyethylene terephthalate can be detected by the automatic analytical device 7 and passed on an appropriate conveying path 12 to a reprocessing stage tailored to polyethylene terephthalate bottles.

Similarly for example, heavily contaminated objects can be detected by the automatic analytical device 7 and, through control of the sorting device 8, be passed to an incineration facility 10, because, due to their heavy contamination, for example due to toxic materials, they are no longer suitable for recovery.

Similarly for refuse objects 2 containing plastics other than polyethylene terephthalate, such as for example polyurethane, polyamide, polyester, polyvinyl chloride, just to mention a few, appropriate recovery methods 11, and 12 indicated by dots, are provided.

With the embodiment illustrated in FIG. 1, the automatic analytical device 7 consists of a positioning device in the form of portal robot 13 through which a probe 14 in the form of a gas pipe can be applied closely to or in contact with a refuse object 15 to be examined. The construction of the probe 14 is described in more detail below. The positioning device 13 is designed to be movable such that the probe 14 can scan or sample any object on the conveyor belt 6. For example, the positioning device exhibits three translationally driven, essentially mutually perpendicular degrees of freedom or axes and at least one rotationally driven axis.

By a monitoring device 16, for example a video camera with subsequent image processing, the position of the object to be examined on the conveyor belt 6 is acquired, and the probe 14 is moved accurately to the refuse object 2 to be examined during the transport of the refuse object 2 on the conveyor device 6.

The probe 14 extracts a sample from the refuse object 15 by vaporizing a small part of the refuse object 15 just analysed. The vapour is passed via a line 17 to a mass spectrometer 18, for example a quadropole broadband mass spectrometer from the company Balzers of type HPA 2000 with a measurement range from 1 amu to 1,000 amu.

In the mass spectrometer the mass spectra of the constituents or fragments of the gas are acquired and passed in the form of a signal via a data line 19 to an evaluation and control unit 20, for example in the form of a computer. In the PC the measured mass spectra are compared with previously determined, stored calibration spectra. The calibration spectra have been, for example, previously obtained from the analysis of objects with a known composition. If the measured mass spectrum matches a saved calibration spectrum, the sorting device 8 is controlled by the control unit 20 according to the composition assigned to the calibration spectrum so that the refuse object can be disposed of in an environmentally friendly manner.

If the refuse object 15 just examined exhibits several polymers as constituents, then the mass spectrum is constituted by the sum of the calibration spectra of these constituents, whereby the proportions of the calibration spectra in the sum are weighted corresponding to the proportion of the constituent in the refuse object. In this way the sorting device 8 can also be controlled in dependence of the determined constituents and their proportions.

The control unit 20 can additionally control the portal robot 13 in dependence of the signals from the monitoring device 16. It is indicated by the especially bidirectional data lines 21, 22.

In the synchronisation of the control of the sorting device 8 to the movement of the refuse objects 2 on the conveyor device 6, the distance of the automatic analytical device 7 from the sorting device 8 and the speed of the conveyor belt 6 or another, equivalent conveying device can be taken into account so that the sorting device is operated when the appropriate refuse object passes during transport.

Figure 2:
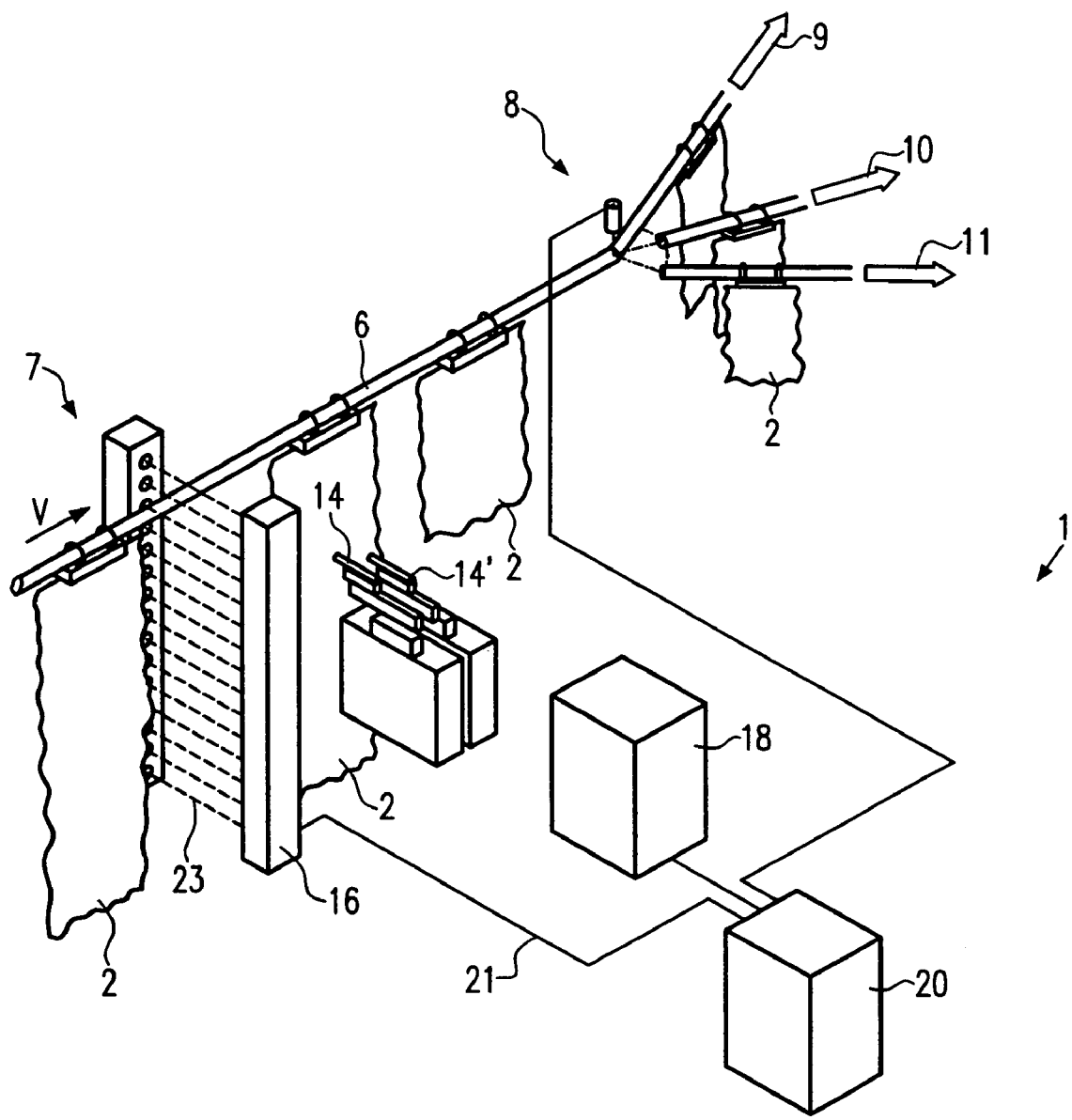
FIG. 2 shows a second embodiment of a refuse recycling plant, in particular for carpets, in a schematic illustration.

FIG. 2 shows a schematic illustration of another plant 1 for the sorting of refuse objects 2 containing polymers, whereby the plant 1 in FIG. 2 is designed specially for the analysis and sorting of carpets.

The carpets 2 are suspended on a conveying device 6 formed as a suspension conveyor and pass the monitoring device 16 which in the embodiment in FIG. 2 is formed as a field of light barriers 23 arranged one above the other.

The carpets 2 pass the monitoring device 16 with a predetermined speed v of the conveyor device 6 and during their passage, depending on their size and shape, they cover part of the light barriers 23. Via the data line 21 the evaluation unit 20 can determine the shape of the carpets 2 based on the signal from the monitoring device 16 and on the conveying speed v, and can position a probe 14 such that it can extract a sample from the carpet surface. A further, identical probe (not shown) can be positioned on the other side of the carpet surface to be able to analyse the front and rear sides simultaneously.

As shown in FIG. 2, two probes 14, 14', which carry out two analyses alternately on the refuse objects 2, can be arranged on each side, respectively, of a carpet 2. In this manner one of the probes—in FIG. 2 this is probe 14'—may be cleaned while the other probe 14 is extracting the sample.

The sample is passed in gaseous form to the mass spectrometer 18, the control and evaluation unit 20 compares the measured mass spectra with the saved calibration spectra and, in dependence of this comparison, operates the sorting device 8 to pass the carpets to different processing stages, 9, 10, 11.

Of course, the control unit and the evaluation unit 20 can also be realised in the form of separate devices which are just connected by data lines.

Figure 3:
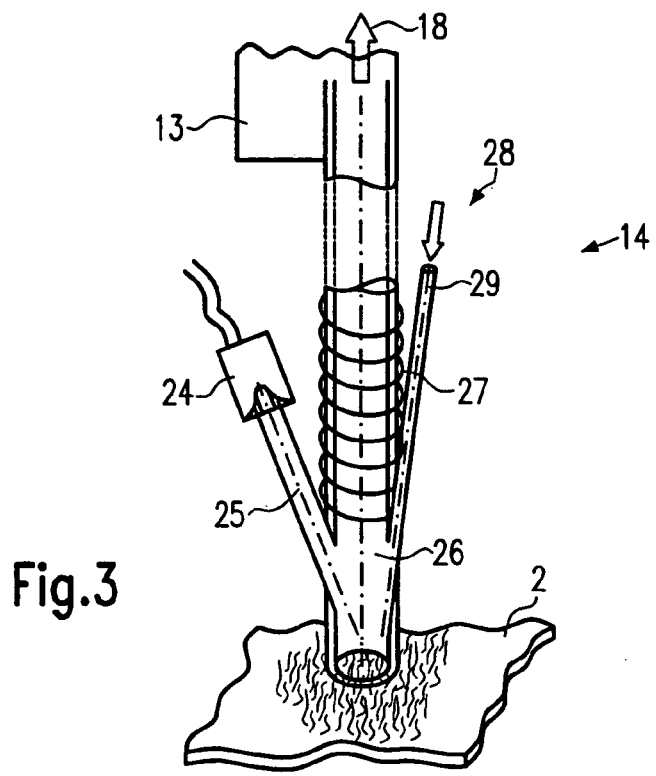
FIG. 3 shows a first embodiment of a probe of an automatic analytical device according to the invention in a schematic illustration.

FIG. 3 shows a schematic detail of a first embodiment of the probe 14 of the automatic analytical device 7.

The probe 14 comprises a vaporisation device 24 in the form of a laser which directs a laser beam 25 onto the refuse object 2 to be examined. Part of the refuse object 2 is vaporised by the laser beam. The vapour is drawn through preferably a capillary shaped probe tube 26 and passed to the mass spectrometer 18 (not shown in FIG. 3).

The probe tube 14 is heated up to a temperature above the condensation point of the vapour generated by the vaporisation device 24 using a probe heater 27. This temperature may be 10° C. or preferably 70° C. above the melting temperature of the plastic of the refuse object 2 or of the component of the refuse object 2 with the highest melting temperature. In particular, the heating temperature to which the probe tube 26 is heated may be above 250° C. and preferably around 270° C.

The probe 14 is, as is just schematically illustrated in FIG. 3, held in a positioning device 13, which for example is designed in the form of a pneumatically or electrically driven multi-axle robot or a placement device.

The positioning device ensures that each refuse object 2 on the conveyor device 6 can be reached by the probe.

Furthermore, the probe 14 comprises a flushing or cleaning device 28 with which the probe 14 is cleaned or flushed when no sample is taken from the refuse objects 2.

The flushing or cleaning device 28 comprises a feed line 29 through which an inert gas can be introduced into the probe tube 27 so that the probe tube is flushed and freed of condensation residues of the vaporised refuse object 2. Preferably, the probe 14 is released from its connection with the mass spectrometer 18 during the flushing stage. In order not to pass the flushing gas into the surroundings, the probe 14 can be connected during the flushing stage to a gas discharge pipe not illustrated in FIG. 2 and by which the flushing gas is purified and/or retained.

In addition the probe heater 27 can be operated as part of the cleaning device in that the probe and capillary tubes 27 are heated to a temperature at which the residues on the wall of the capillary or probe tube and in the interior of the probe tube are incinerated. In order to maintain a high measurement accuracy also with a large number of measurements, it is of advantage if during the complete time in which the probe 14 is not taking any samples, flushing with the flushing gas occurs.

The flushing gas can also be heated to a temperature which leads to incineration of the residues in the capillary tube and the temperature of the inert gas is preferably above the condensation temperature of the vapour generated by the vaporisation device 24.

Figure 4:
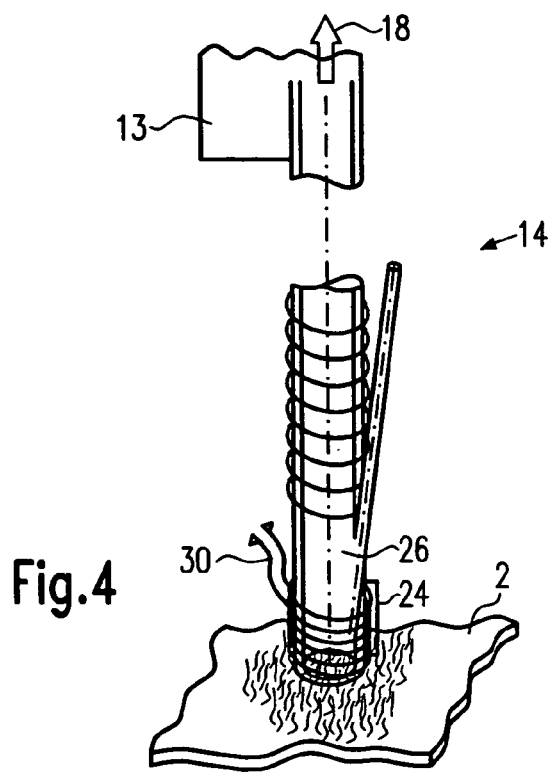
FIG. 4 shows a second embodiment of a probe of an automatic analytical device according to the invention in a schematic illustration.
Figure 5:
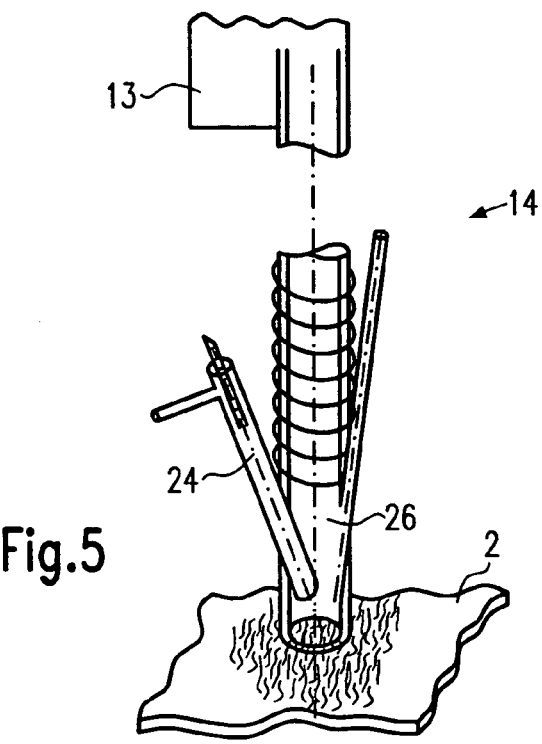
FIG. 5 shows a further embodiment of a probe of an automatic analytical device according to the invention in a schematic illustration.

In FIGS. 4 and 5 two further embodiments of the probe 14 are described which can be used as alternative or supplementary forms of the embodiment of FIG. 3. For the sake of simplicity, in the following only the differences to the embodiment in FIG. 3 are considered.

In FIG. 4 the vaporisation device 24 is designed as an electrical heating device which is arranged in a section of the probe 14 which comes into contact with the refuse object 2, preferably therefore at the mouth of the capillary tube 26. The temperature of the vaporisation device 24 is held constant by a closed-loop control device 30 which is only illustrated schematically.

The embodiment in FIG. 4 has the advantage that, by the vaporisation device 24 on the mouth, this region can be cleaned in a double function in that the vaporisation device 24, when no samples are taken, is taken up to a heating temperature at which the residues in the mouth region of the capillary tube 26 incinerate. In particular the mouth region is surprisingly susceptible to deposits of the vaporised refuse object 2, which can impair the following measurements.

In the embodiment of FIG. 5 a gas burner is used as the vaporisation device 24 to which combustion gas is passed via a feed line 31. This embodiment is inexpensive, but has the disadvantage that due to reactions with the combustion gas and due to the combustion gas itself, measurements are more difficult to evaluate.

In all the embodiments, the capillary tube 26 may be made from corrosion resistant steel with a polished inner side or from glass.

Figure 6:
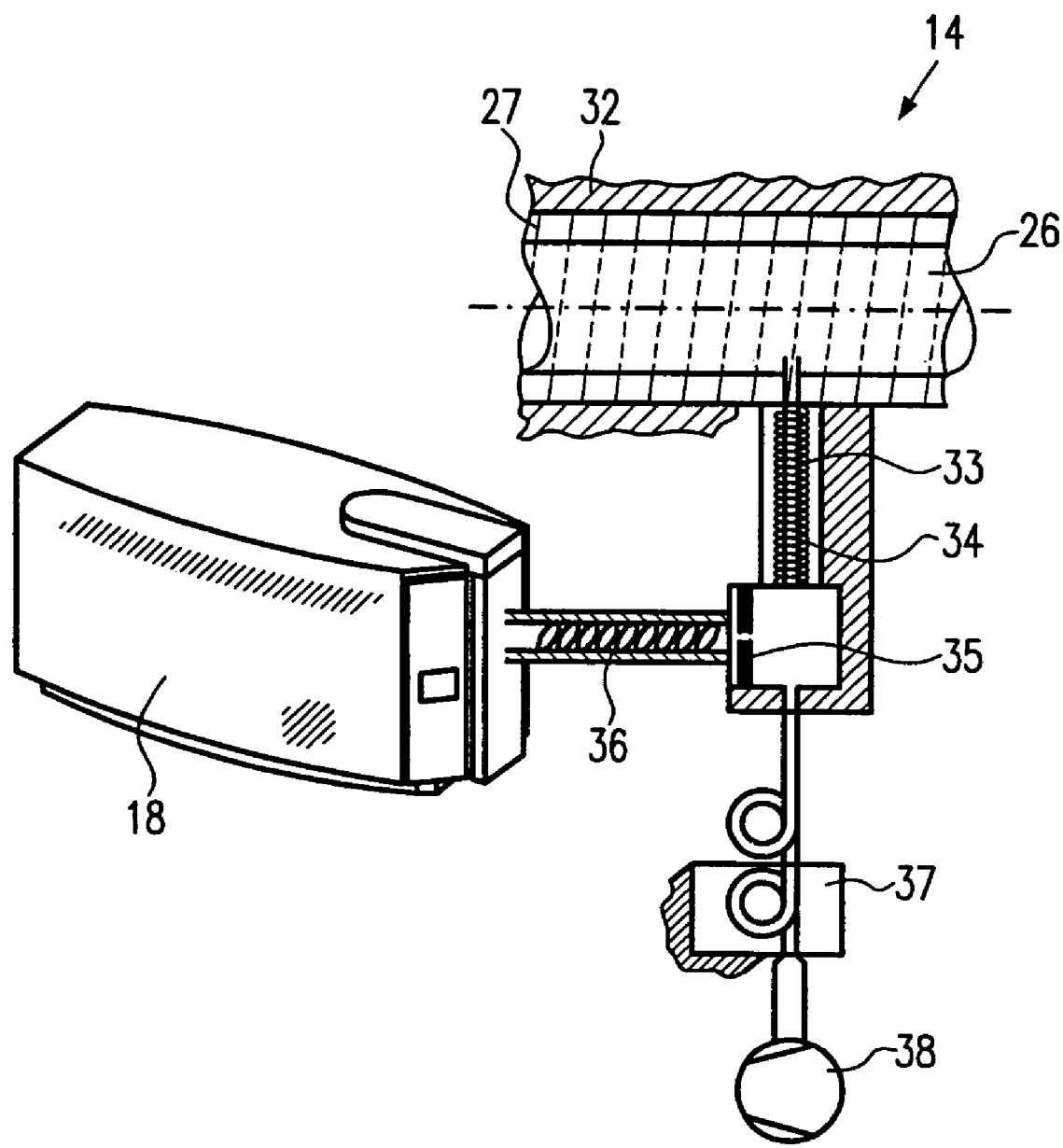
FIG. 6 shows a pipe system of an automatic analytical device according to the invention in a schematic illustration.

In FIG. 6 an embodiment of the connection between the probe 14 and the mass spectrometer 18 is schematically illustrated.

As can be seen in FIG. 6, the capillary tube 26 with the heating device 27 can be enclosed in thermal insulation 32 so that the wall temperature is maintained as constant as possible. In addition, an inert gas such as helium gas or nitrogen can be supplied to the vapour of the refuse object 2 (not shown in FIG. 6), for example, through the flushing gas line 29, to dilute the gas sample.

The sample vapour is drawn off from the capillary tube 26 through a suction capillary 33. The suction capillary 33 is provided with another heating device 34 and is essentially heated to the same temperature as the probe line 26. The probe gas is passed through a feed capillary 36 to the mass spectrometer 18, where the mass spectrum of the gas sample is determined, via a measurement orifice 35, which ensures a predetermined volume flow and which is also heated to avoid condensation of the sample gas.

The sample gas is tapped off from a multistage vacuum pump 38 or an ion pump via a cooling trap 37 and disposed of, for example by incineration.

Figure 7:
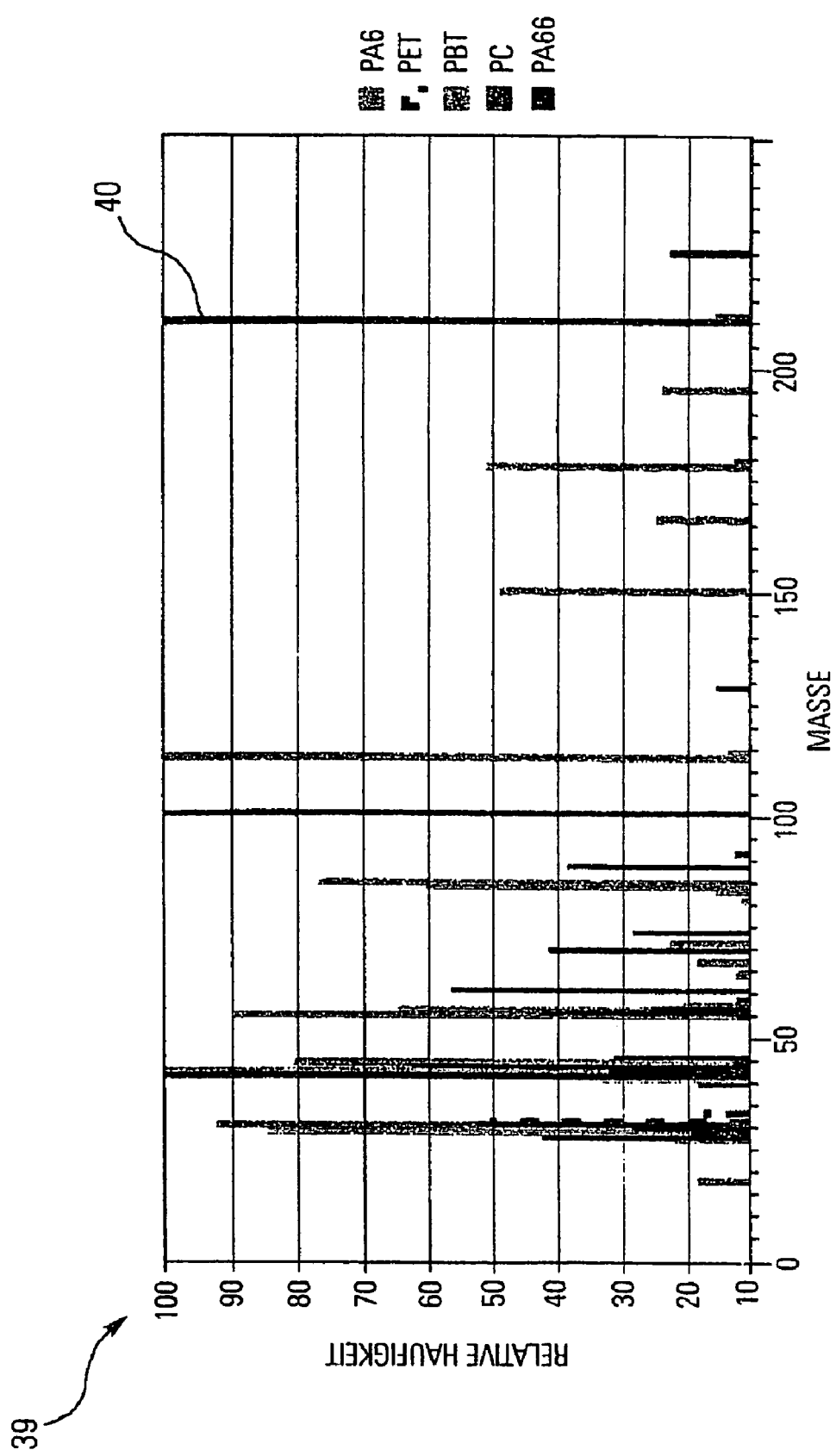
FIG. 7 shows a schematic illustration of a mass spectrum for the analysis of the composition of a refuse object.

FIG. 7 shows a typical mass spectrum 40 of a carpet residue. The mass spectrum is here also designated as a fragmentation spectrum, because in the mass spectrometer the polymers are cracked into constituents, the so-called fragments. The ratio of the mass to the charge of the ionised fragments is determined by the mass spectrometer. Each polymer is characterised here by a certain combination and by a certain relative frequency of the fragments. Therefore, the fragmentation spectra are particularly suitable as calibration spectra.

In the example schematically illustrated in FIG. 7 the carpet residue contains the polymers polyamide 6 (PA 6), polyethylene terephthalate (PET), polybutylene terephthalate (PBT), polycarbonate (PC) and polyamide 6,6 (PA 6,6). As can be seen in FIG. 7, these polymers sometimes exhibit the same fragments, and sometimes different fragments, which can be recognised from the position of the peaks on the x axis labelled "Mass": If peaks are located at the same point, then the polymers exhibit the same constituents. Since however the proportion of the individual fragments in the polymers is different, the height of the peaks, i.e. the relative frequency of these fragments in the polymers, is different.

Since the composition is determined in advance for each polymer using calibration spectra and as a mass spectrum of any refuse object 2, as shown in FIG. 7, is composed of a linear combination, i.e. an addition, of the individual fragmentation spectra of the pure polymers in dependence of their frequency in the refuse object 2, the composition of the complete refuse object 2 can be determined in a simple manner by mass spectroscopy by solving of a linear equation system.

This method is so fast and so reliable that according to the invention the method can be used for the online analysis of refuse objects in recycling plants.

The invention claimed is:

1. A method by which refuse objects containing polymers are analyzed before recycling with regard to the polymers they contain during transport, the method comprising: converting a part of the refuse object into the gaseous state; mass spectroscopically examining a part of the refuse object by a mass spectrometer; and sorting the refuse object in dependence of the result of the mass spectroscopic examination, wherein a gas line is automatically cleaned after a sample extraction by being flushed with an inert gas, whereby the gas line is released from its connection with the mass spectrometer during flushing.

2. The method according to claim 1, wherein a mass spectrum automatically acquired in the course of the mass spectroscopic examination is automatically compared to saved calibration spectra representative of polymers and that the refuse object is sorted depending on this comparison.

3. The method according to claim 2, wherein the maxima and their position in the measured mass spectrum are compared with the maxima of the calibration spectra.

4. The method according to claim 1, wherein the mass spectra are acquired over a range from 1 amu to 2,000 amu.

5. The method according to claim 1, wherein the gas is drawn through a gas line into the mass spectrometer.

6. The method according to claim 5, wherein the gas line is heated.

7. The method according to claim 5, wherein the line is at a temperature of at least 10° C. above the melting point of the polymer or of the highest melting component of the refuse object.

8. The method according to claim 7, wherein the line is heated to a temperature of at least 70° C. above the melting point of the polymer or of the highest melting component of the refuse object.

9. The method according to claim 6, wherein the temperature of the line is controlled to at least 250° C.

10. The method according to claim 1, wherein the gas flow passed to the mass spectrometer is diluted by an inert gas.

11. The method according to claim 1, wherein the inert gas is heated.

12. The method according to claim 1, wherein a mass spectroscopic examination is carried out with another gas line during the flushing of the gas line.

13. The method according to claim 1, wherein the refuse objects are analyzed during transport by a conveyor device of the plant.

14. The method according to claim 1, wherein the refuse object is sorted in dependence of the result of the mass spectroscopic examination.

15. An automatic analytical device, which is designed for installation in a plant for the recycling of refuse objects containing polymers, comprising:
a probe, which comprises a vaporization device and a gas line and a suction capillary, whereby a part of the refuse object can be vaporized by the vaporization device and whereby the gas line is adapted to be connected to a mass spectrometer and the gas can be fed through the gas line to the mass spectrometer for acquisition of a mass spectrum, whereby the suction capillary is adapted to pass the probe gas from the gas line to the mass spectrometer and is adapted to release the gas line from its connection with the mass spectrometer between measurements;
an evaluation unit, which is adapted to be connected for the transfer of data to the mass spectrometer and through which a signal representative of the composition of the refuse object can be output in dependence of the acquired mass spectrum; and
a sorting device, which is adapted to be operated by the evaluation unit in dependence of the signal, further comprising a flushing device, through which an inert gas can be passed through the gas line between measurements.

16. The automatic analytical device according to claim 15, further comprising a heating device through which the gas line can be heated.

17. The automatic analytical device according to claim 15, further comprising a closed-loop control system through which the temperature of the gas line can be controlled to an adjustable specified set value.

18. The automatic analytical device according to claim 15, further comprising a position device, through which the probe can be automatically moved to a refuse object.

19. The automatic analytical device according to claim 15, wherein the vaporization device comprises a laser which can be directed onto the refuse object.

20. A method by which refuse objects containing polymers are analyzed before recycling with regard to the polymers they contain during transport, the method comprising: converting a part of the refuse object into the gaseous state; mass spectroscopically examining a part of the refuse object by a mass spectrometer; sorting the refuse object in dependence of the result of the mass spectroscopic examination; drawing a gas alternately through a first and second gas line into the mass spectrometer; and carrying out a mass spectroscopic examination with the first gas line while the second gas line is cleaned, whereby the respective gas line is released from its connection with the mass spectrometer during flushing.

21. The method according to claim 20, wherein the gas is drawn through a heated gas line into the mass spectrometer.

22. The method according to claim 21, wherein the line is at a temperature of at least 10° C. above the melting point of the polymer or of the highest melting component of the refuse object.

23. The method according to claim 22, wherein the line is heated to a temperature of at least 70° C. above the melting point of the polymer or of the highest melting component of the refuse object.

24. The method according to claim 21, wherein the temperature of the line is controlled to at least 250° C.

25. The method according to claim 20, wherein the gas flow passed to the mass spectrometer is diluted by an inert gas.

26. The method according to claim 20, wherein the refuse objects are analyzed during transport by a conveyor device of the plant.

27. An automatic analytical device, which is designed for installation in a plant for the recycling of refuse objects containing polymers, comprising:

a probe, which comprises a vaporization device and a gas line and a suction capillary, whereby a part of the refuse object can be vaporized by the vaporization device and whereby the gas line is adapted to be connected to a mass spectrometer and the gas can be fed through the gas line to the mass spectrometer for acquisition of a mass spectrum, whereby the suction capillary is adapted to pass the probe gas from the gas line to the mass spectrometer and is adapted to release the gas line from its connection with the mass spectrometer between measurements;

an evaluation unit, which is adapted to be connected for the transfer of data to the mass spectrometer and through which a signal representative of the composition of the refuse object can be output in dependence of the acquired mass spectrum; and a sorting device, which is adapted to be operated by the evaluation unit in dependence of the signal, the automatic analytical device further comprising:

a second probe, which comprises a vaporization device and a gas line and a suction capillary, whereby a part of the refuse object can be vaporized by the vaporization device and whereby the gas line is adapted to be connected to the mass spectrometer and the gas can be fed through the gas line to the mass spectrometer for acquisition of a mass spectrum, whereby the suction capillary is adapted to pass the probe gas from the gas line to the mass spectrometer and is adapted to release the gas line from its connection with the mass spectrometer between measurements; and a flushing device, through which a cleaning gas can be passed through the gas line of one of said probe or said second probe while it is between measurements and is not connected to said mass spectrometer.

28. The automatic analytical device according to claim 27, further comprising a heating device through which the gas line of the probe or the second probe can be heated.

29. The automatic analytical device according to claim 27, further comprising a closed-loop control system through which the temperature of the gas line of the probe or the second probe can be controlled to an adjustable specified set value.

30. The automatic analytical device according to claim 27, further comprising a position device, through which the probes can be automatically moved to a refuse object.

* * * * *